US009555911B2

(12) United States Patent
Pawlowski et al.

(10) Patent No.: US 9,555,911 B2
(45) Date of Patent: Jan. 31, 2017

(54) PROCESS FOR HANDLING OR PROCESSING CONTAINERS FOR MEDICAL OR PHARMACEUTICAL APPLICATIONS AND CARRIER AND TRANSPORT OR PACKAGING CONTAINER THEREOF

(71) Applicant: SCHOTT AG, Mainz (DE)

(72) Inventors: Edgar Pawlowski, Stadecken-Elsheim (DE); Kai Wissner, Mainz (DE); Ralph Lovis, Winterthur Schwiez (CH)

(73) Assignee: SCHOTT AG, Mainz (DE)

( * ) Notice: Subject to any disclaimer, the term of this patent is extended or adjusted under 35 U.S.C. 154(b) by 529 days.

(21) Appl. No.: 13/886,730

(22) Filed: May 3, 2013

(65) Prior Publication Data

US 2014/0027342 A1    Jan. 30, 2014

(30) Foreign Application Priority Data

May 3, 2012  (DE) ........................ 10 2012 103 901
Nov. 29, 2012 (DE) ........................ 10 2012 111 624

(51) Int. Cl.
*A61J 1/00*    (2006.01)
*B65B 43/08*   (2006.01)
(Continued)

(52) U.S. Cl.
CPC ................. *B65B 43/08* (2013.01); *A61J 1/14* (2013.01); *A61M 5/001* (2013.01); *A61M 5/008* (2013.01);
(Continued)

(58) Field of Classification Search
CPC .................................. B65D 85/70; A61J 1/00
See application file for complete search history.

(56) References Cited

U.S. PATENT DOCUMENTS 832,086 A     10/1906  Schweitzer
2,598,492 A    5/1952  Boes
(Continued)

FOREIGN PATENT DOCUMENTS

DE     8805580.7 U1    8/1988
DE     10212734 A1    10/2003
(Continued)

*Primary Examiner* — Sean E Conley
*Assistant Examiner* — Donald Spamer
(74) *Attorney, Agent, or Firm* — Ohlandt, Greeley, Ruggiro & Perle, LLP

(57) ABSTRACT

A process for the treatment or processing of containers is provided. The process includes automatically conveying the containers past a processing station for the treatment or processing by or through a conveying device and then inserting the containers into a transport or packaging container having a bottom, a circumferential side wall and an insertion opening opposite to the bottom. In some embodiments, a plurality of containers are placed on a flat supporting base so that the bottoms of the containers directly rest on the flat supporting base; the containers, while resting on the flat supporting base, are conveyed to a processing station by the conveying device to be treated or processed; and after the treatment or processing of the containers, the transport or packaging container is placed on the flat supporting base so that all the containers of the plurality of containers are accommodated in the transport or packaging container.

13 Claims, 18 Drawing Sheets

(51) Int. Cl.
  *A61M 5/00*   (2006.01)
  *B01L 9/06*   (2006.01)
  *A61J 1/14*   (2006.01)
  *B65D 85/00*  (2006.01)
  *B65B 55/02*  (2006.01)
  *B65B 63/08*  (2006.01)
  *B65B 3/00*   (2006.01)

(52) U.S. Cl.
  CPC .................. *B01L 9/06* (2013.01); *B65B 3/003* (2013.01); *B65B 55/025* (2013.01); *B65B 63/08* (2013.01); *B65D 85/70* (2013.01); *A61M 2207/00* (2013.01); *B01L 2200/18* (2013.01); *B65B 2220/24* (2013.01)

(56) References Cited

U.S. PATENT DOCUMENTS

| | | | |
|---|---|---|---|
| 3,537,189 | A | 11/1970 | Bender |
| 4,444,310 | A | 4/1984 | Odell |
| 5,128,105 | A | 7/1992 | Berthold et al. |
| 5,483,843 | A | 1/1996 | Miller et al. |
| 5,964,043 | A | 10/1999 | Oughton et al. |
| 6,341,490 | B1 | 1/2002 | Jones |
| 8,100,263 | B2 | 1/2012 | Vanderbush et al. |
| 8,118,167 | B2 | 2/2012 | Togashi et al. |
| 8,469,185 | B2 | 6/2013 | Nicoletti |
| 2003/0168370 | A1* | 9/2003 | Merboth .................. A01N 1/02 206/438 |
| 2005/0013745 | A1 | 1/2005 | Buchanan et al. |
| 2005/0147773 | A1* | 7/2005 | Saliaris .............. B65D 41/0414 428/34.1 |
| 2009/0238727 | A1 | 9/2009 | Sinclair et al. |
| 2011/0132797 | A1 | 6/2011 | Adair et al. |

FOREIGN PATENT DOCUMENTS

| | | |
|---|---|---|
| EP | 1339342 A2 | 9/2003 |
| EP | 2 420 450 A1 | 2/2012 |
| WO | 96/29556 | 9/1996 |
| WO | 0242164 A2 | 5/2002 |
| WO | 2009015862 A1 | 2/2009 |
| WO | 2010086128 A1 | 8/2010 |
| WO | 2011007194 A1 | 1/2011 |
| WO | 2011015896 A1 | 2/2011 |
| WO | 2011110872 A1 | 9/2011 |
| WO | 2011135085 A1 | 11/2011 |
| WO | WO2011135085 * | 11/2011 |
| WO | 2012007056 A1 | 1/2012 |
| WO | 2012025549 A1 | 3/2012 |

* cited by examiner

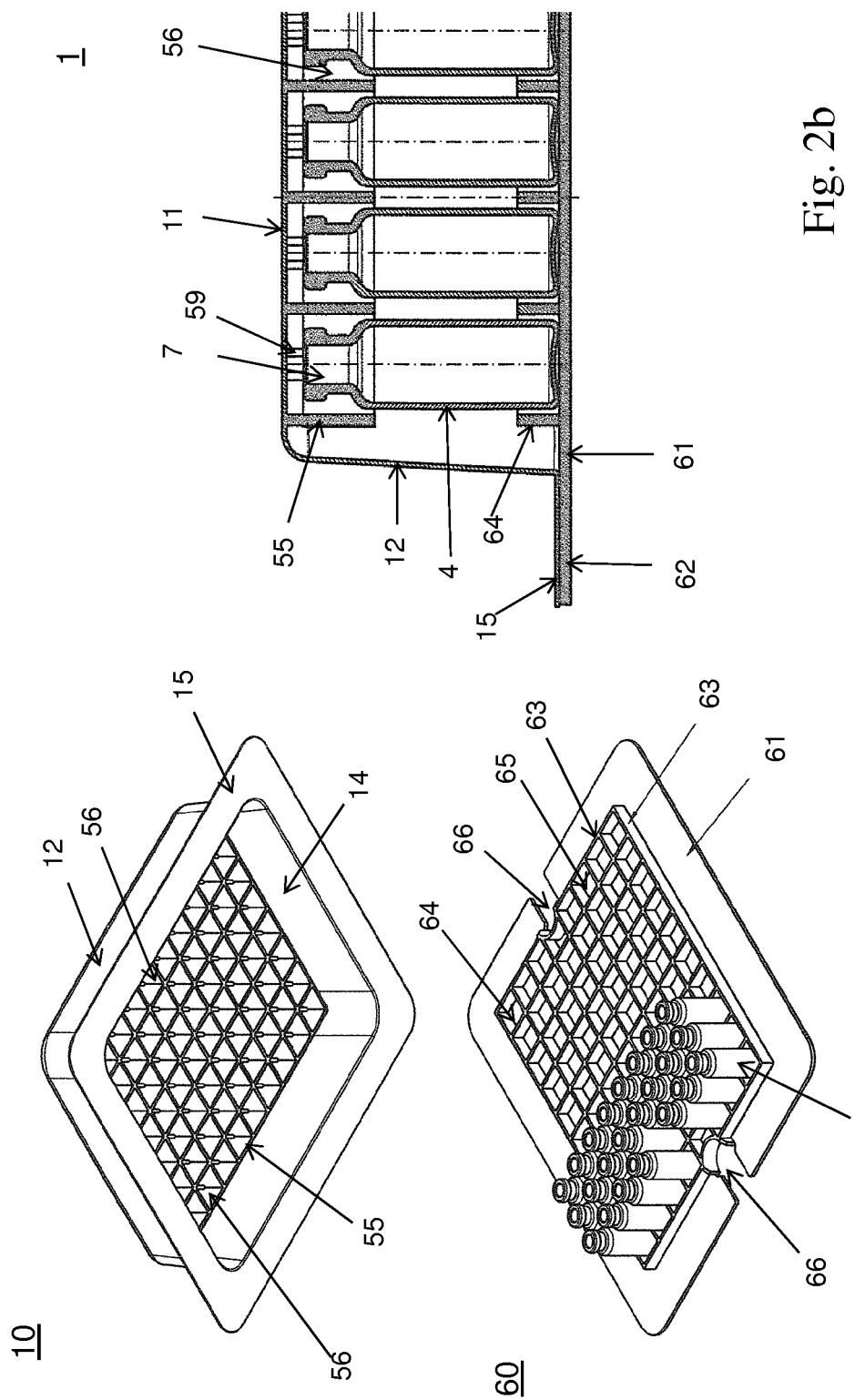

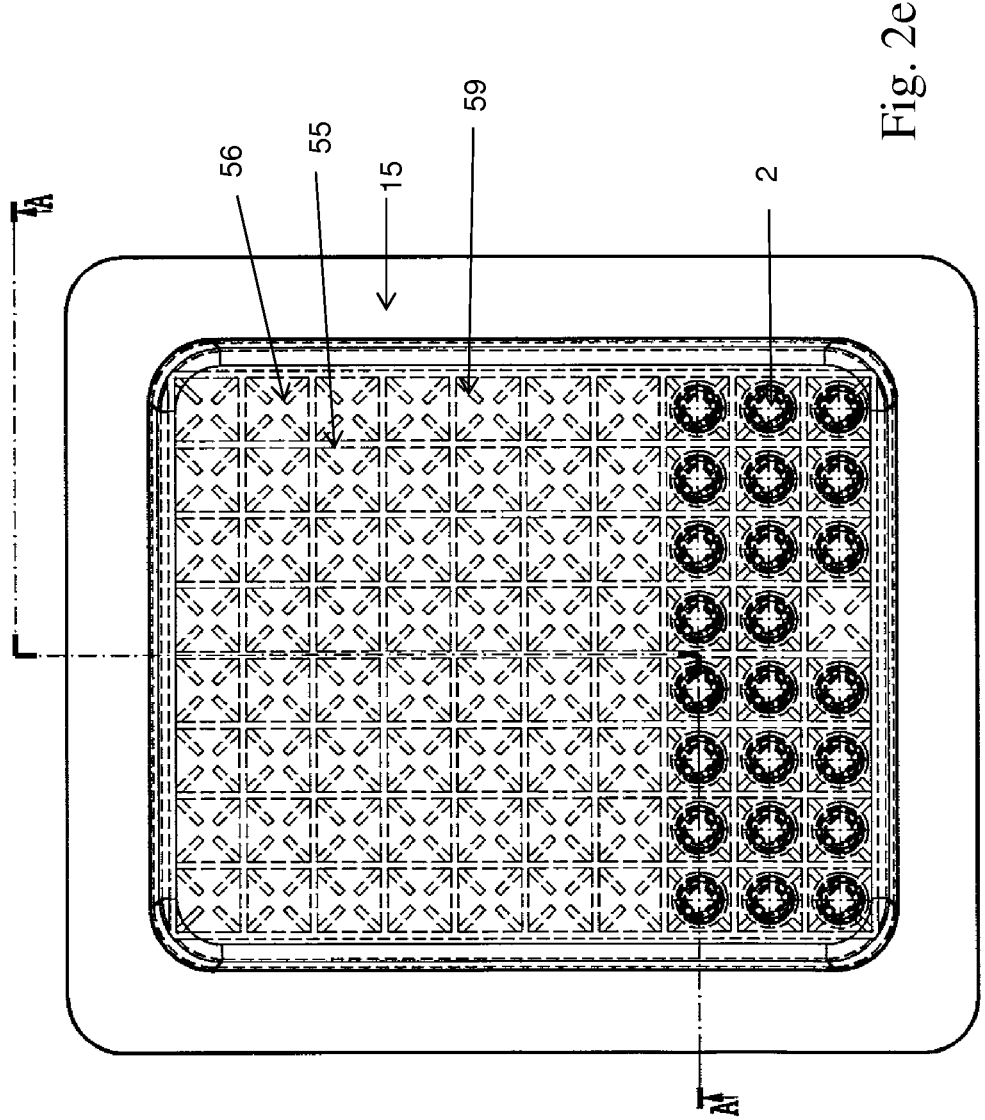

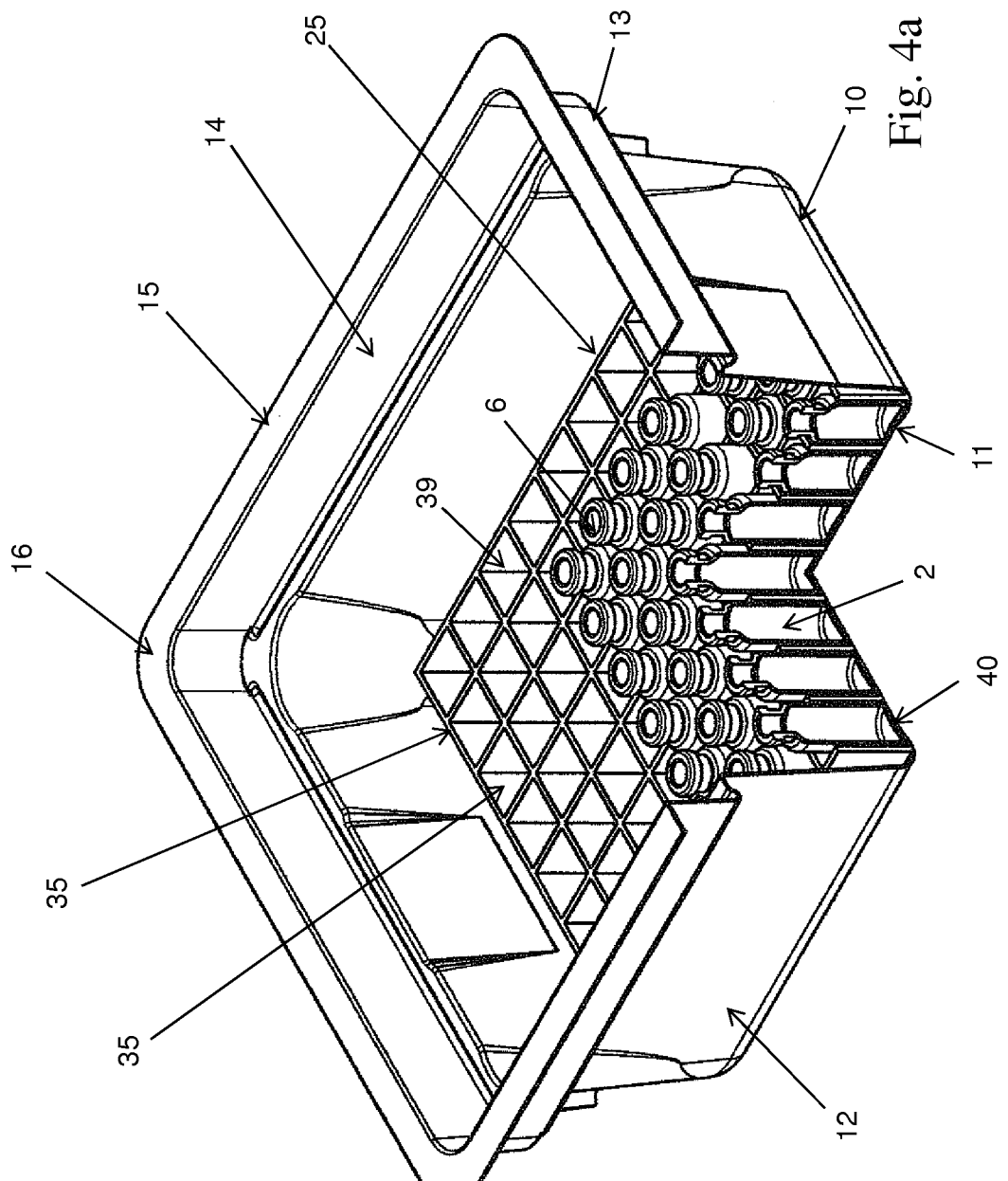

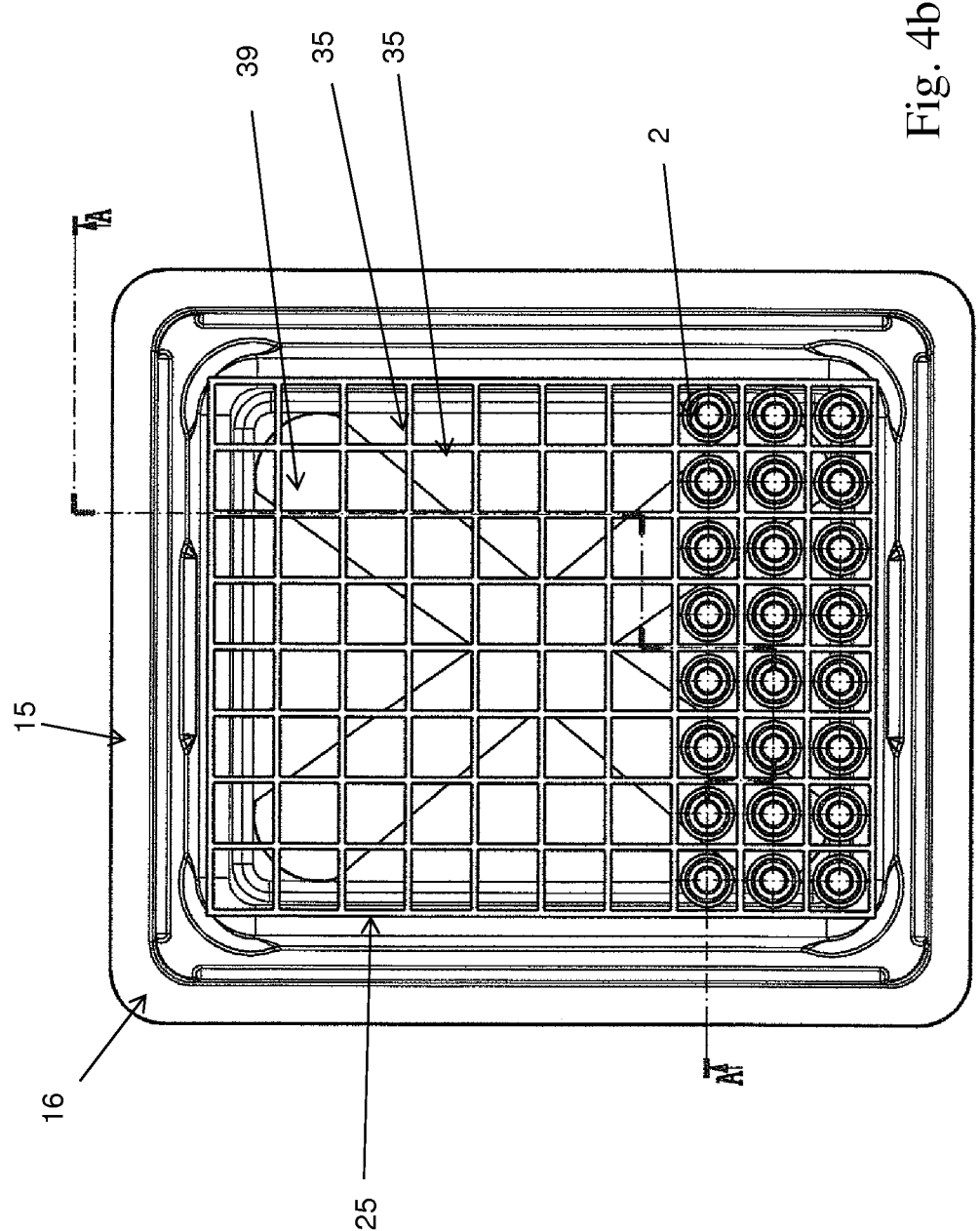

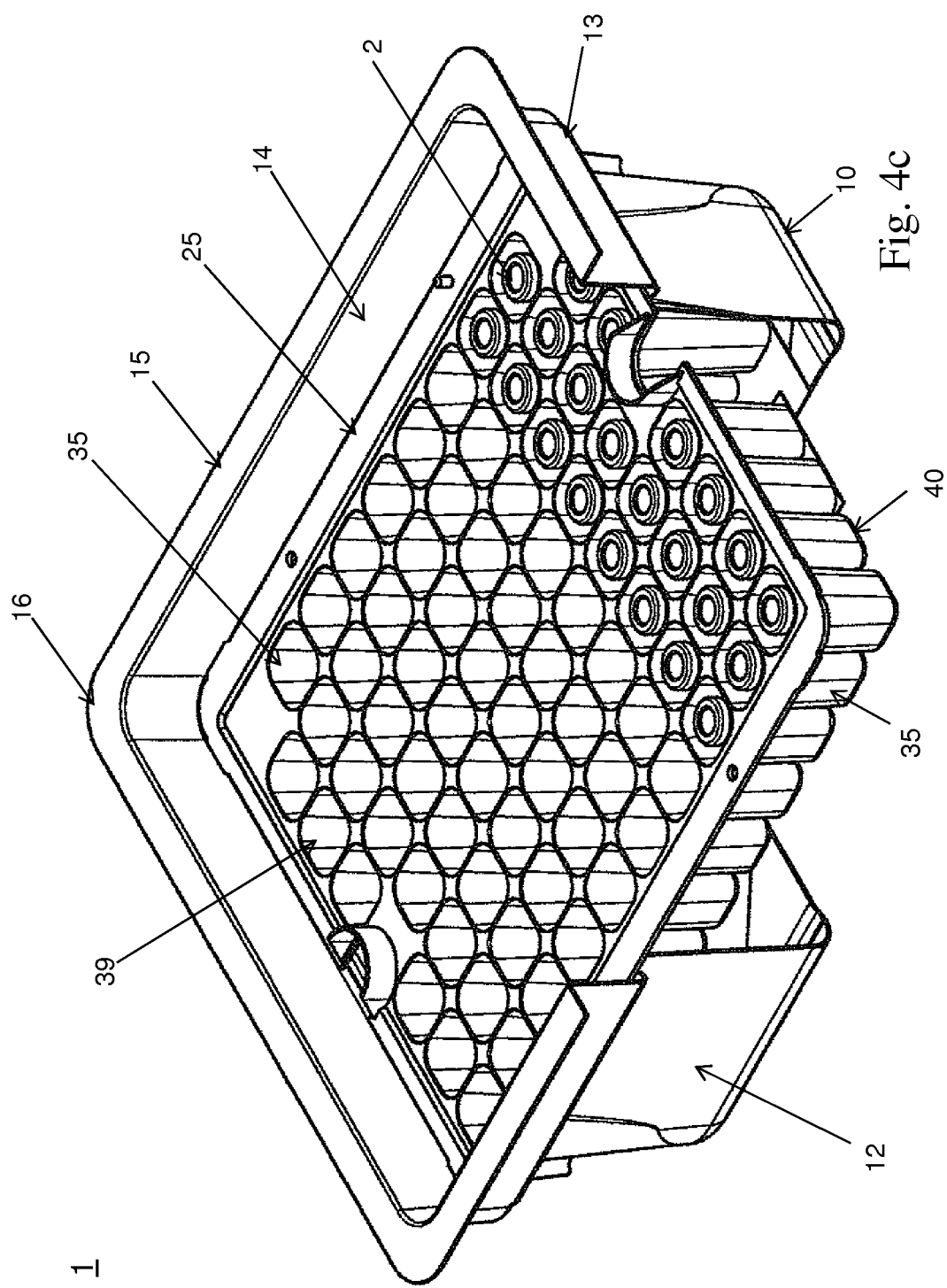

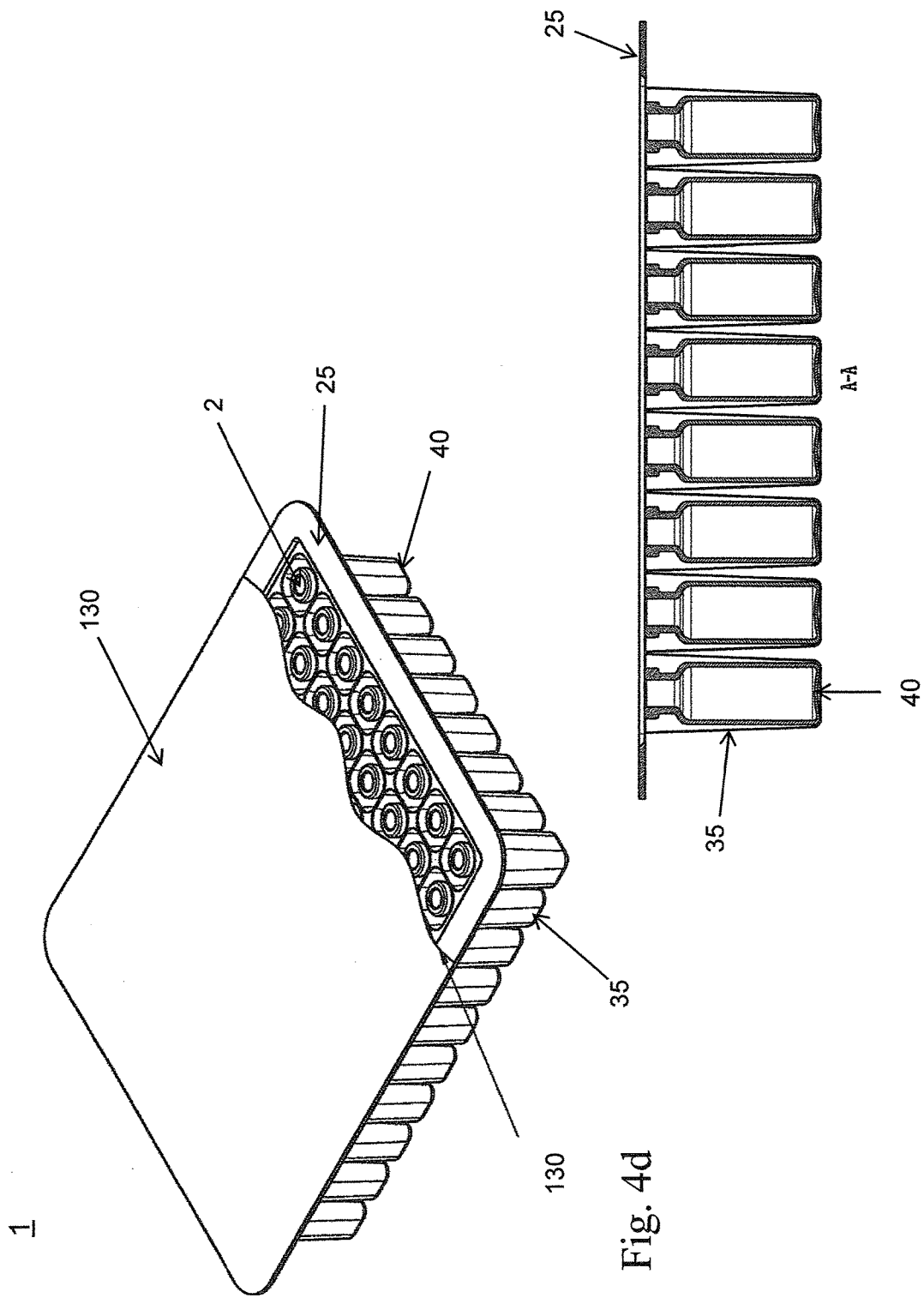

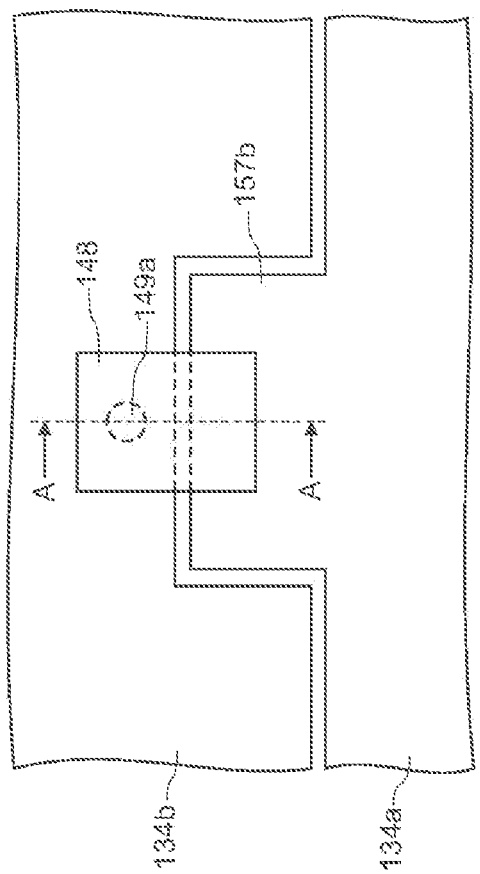
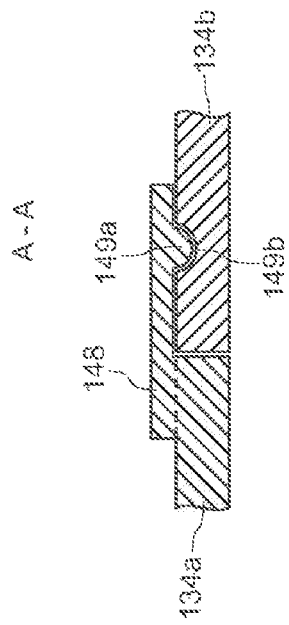
Fig. 7d
Fig. 7e

PROCESS FOR HANDLING OR PROCESSING CONTAINERS FOR MEDICAL OR PHARMACEUTICAL APPLICATIONS AND CARRIER AND TRANSPORT OR PACKAGING CONTAINER THEREOF

The present application claims the priority of the German patent applications No. 10 2012 103 901.1 and 10 2012 111 624.5, "Holding structure for concurrently holding a plurality of medical or pharmaceutical containers and transport containers or packaging container with the same", filed on 3 May 2012 and 29 Nov. 2012, respectively, the entire contents of which are hereby expressly incorporated by way of reference.

FIELD OF THE INVENTION

The present invention generally relates to the concurrent treatment or processing of a plurality of containers for the storage of agents for medical, pharmaceutical or cosmetic applications, in particular of flasks (vials), and more particularly to the concurrent automated conveyance and transfer of a plurality of containers at process stations, such as a filling or processing plant, a sterile tunnel, a freeze-dryer for lyophilizing of a liquid containing an active agent or the like. Further aspects of the present invention relate to a flat supporting base and a transport or packaging container for this purpose.

BACKGROUND OF THE INVENTION

Medication containers, for example vials, carpoules or ampoules, are widely used as containers for preservation and storage of medical, pharmaceutical or cosmetic preparations to be administered in a liquid form, in particular in pre-dosed amounts. These generally have a cylindrical shape, can be made of plastic or glass and are available in large quantities at low costs. In order to fill the containers under sterile conditions as efficiently as possible concepts are increasingly used according to which the containers are already packaged in a transport or packaging container at the manufacturer of the containers under sterile conditions, which are then unpacked and further processed at a pharmaceutical company under sterile conditions, in particular in a so-called sterile tunnel.

For this purpose various transport or packaging containers are known from the prior art, in which a plurality of medication containers are concurrently arranged in a regular array, for example in a matrix array along rows and columns extending perpendicular thereto. This has advantages with regard to the automated further processing of the containers since the containers can be passed at controlled positions and in a predetermined arrangement at processing stations, for example to processing machines, robots or the like.

Examples for such transport or packaging containers are disclosed in U.S. Pat. No. 8,118,167 B2 and U.S. Pat. No. 8,100,263 B2. Further similar transport or packaging containers and supporting bases are disclosed in WO 2011/135085 A1, US 2011/0277419 A1, WO 2012/025549 A1, WO 2011/015896 A1, WO 2012/007056 A1 and WO 2009/015862 A1.

A conventional transport or packaging container, similar to that disclosed in EP 2 382 135 B1 (corresponding to WO 2010/086128) is shown in FIG. 1a. The containers $2'$ are received in an insert having a plurality of cylindrical receptacles $39'$ formed therein, which are formed by transverse webs $35'$ and a bottom $40'$. The bottoms $3'$ of the containers $2'$ rest on the bottom $40'$ of the insert, the filling openings $7'$ at the upper end of the containers $2'$ face the opening of the transport or packaging container $10$. The insert is inserted into the transport or packaging container $10'$ together with the plurality of containers $2'$ and constitutes a separate member.

However, for the further processing the medication containers must always be separated. This is exemplified with reference to FIG. 1b, which is a schematic flow diagram of a conventional process for freeze-drying of pharmaceutical products in medication containers, e.g. of the kind disclosed in U.S. Pat. No. 5,964,043.

First, the processing plant, namely a sterile tunnel, is charged with the vials. For this purpose, the vials are mounted upside down in transport frames, which are then conveyed through the processing plant. For pretreatment the vials held in the transport frame are sterilized. Then the transport frames together with the vials stored therein are turned and filled with a drug solution.

Subsequently a plug is placed on the upper edge of the vial, in which a passage is formed, via the interior of the vials is communicating with the cavity of the freeze-dryer during the lyophilization.

For freeze-drying (also known as lyophilization, or sublimation drying) the vials are then removed from the transport frame and individually put into the freeze-dryer. For this purpose, the bottoms of the vials must be put directly on a cooling bottom of a planar design to obtain a good cooling effect. If a direct contact is not ensured over the entire surface at this stage, this will result in a considerable prolongation of the freeze-drying process, leading to higher costs.

After freeze-drying the vials are removed from the freeze-dryer, the plugs are pushed down and a metal cap is put on the plug and beaded or crimped. Vials processed in such manner are then delivered, for example by inserting a plurality of vials together in a supporting base and inserting the supporting base into a transport or packaging container, which is then packed sterilely for delivery.

The direct contact between the bottom of the medication containers and the cooling bottom necessary for freeze-drying conventionally requires treatment or processing of individual containers, which increases the processing and packaging costs. Conventionally a batch-wise, concurrent processing of a plurality of medication containers is not possible. In any case, a direct contact between the bottoms of the medication containers, in particular of the bottoms of the vials is not possible in the conventional supporting bases.

In particular, due to the necessary separation the above described procedure is time consuming and expensive.

SUMMARY OF THE INVENTION

It is an object of the present invention to further enhance a process for treatment or processing of containers, which are to be used for storage of agents for cosmetic, medical or pharmaceutical applications or which contain them, such that it can be performed more quickly and more economical, more automated and reliable. According to further aspects of the present invention, a flat supporting base and a transport or packaging container are to be provided for this purpose.

According to the present invention these problems are solved by a process with the features of claim 1, a use of a flat supporting base of claim 15 and a transport or packaging container of claim 16. Further advantageous embodiments are the subject-matter of the dependent claims.

According to the present invention, a process for the treatment or processing of containers is provided, which serve for storing substances for cosmetic, medical or pharmaceutical applications or contain them, in particular of flasks (vials), wherein the containers are designed to be open at one end, wherein the containers are automatically conveyed past a processing station by means of a conveying device for treatment or processing or through it, and the containers are then inserted into a transport or packaging container having a bottom, a circumferential side wall and an insertion opening opposite to said bottom, in which process:

a plurality of containers are placed on a flat supporting base in a predetermined arrangement, so that the bottoms of the containers rest directly on the flat supporting base; the containers, while resting on the flat supporting base, are conveyed to a processing station by said conveying device in order to be treated or processed there; and the transport or packaging container is arranged on the flat supporting base after the treatment or processing of the containers such that all containers of the plurality of containers are accommodated in the transport or packaging container. Subsequently the transport or packaging container is closed or sealed. In particular, the transport or packaging container is placed directly on the flat supporting base in order to directly close or seal it.

Because the bottoms of the containers rest directly on the flat supporting base, it is possible to treat or process the containers in an upright position. In this orientation, the containers can then be inserted into the transport or packaging container, without requiring them to be turned over. This surprisingly simple measure minimizes the risk that the containers are damaged due to shocks or collisions with each other or that their arrangement is changed accidentally, for instance by vibration or the like. Because the bottoms of the containers can rest directly on the bottom of the flat supporting base during the treatment or processing, according to the present invention also an excellent thermal contact with a supporting surface can be accomplished for the flat supporting base, in particular with a metal surface, for example of a freeze-dryer. To this end, the flat supporting base is preferably formed of a material having a high thermal conductivity and with a minimum material thickness and the back of the flat supporting base, which is facing the supporting surface during the intended use, is formed as plane as possible or exactly in correspondence to the surface of this supporting surface in order to ensure a full-surface contact between the supporting surface and the flat supporting base.

For receiving the containers in the transport or packaging container the latter is simply put over the flat supporting base or placed on it after the treatment or processing, without the necessity that the flat supporting base must be moved or turned over for this purpose.

According to a further embodiment, positioning means are formed on the bottom of the flat supporting base or of the transport or packaging container, which cooperate with the containers so as to define the predetermined arrangement of the plurality of containers. The positioning means on the flat supporting base can maintain the predetermined arrangement even during treatment or processing of the containers. The positioning means may be provided in particular in the form of projections having a suitable profile, which protrude preferably perpendicularly from the surface of the flat supporting base or from the bottom of the transport or packaging container and which act as stops or limits for restricting or limiting a lateral displacement of the containers in a suitable manner. For this purpose, the height of these protrusions generally may also be significantly less than the axial length of the containers. In particular, these respective projections may also be formed as circumferential projections to form a cylindrical or polygonal receptacle, if viewed in a plan view, in which the container can be partially received. The side walls of these receptacles can abut directly on the side walls of the containers or even clamp them slightly. Generally, however, the positioning means and side walls may also be configured such that the containers are received loosely by them. In this manner, in particular a collision of directly adjacent containers can be prevented, as they rest on the flat supporting base or are accommodated in the transport or packaging container.

According to a further embodiment, openings are formed between the positioning means through which a lifting device may extend to lift the containers for treatment or processing to a raised position in or at the processing station, in which the bottoms of the containers do not directly rest on the flat supporting base. Thus, also additional process steps may be performed which require such a raised position, for example for filling the containers, for optical inspection of the contents of the containers or the like. The lifting device can thus act on the bottom side of the containers to raise them and lower them again, so that the intrusion of mechanical wear into the inner volume of the containers can be reliably prevented. The lifting device may for example be formed as a vertically adjustable lifting arm or lifting rod, which extends through the openings of the flat supporting base and is brought in contact with the bottom of the container to lift this container.

According to a further embodiment, the containers continue cooperating with the positioning means in the raised position so that the predetermined arrangement continues to be fixed by the positioning means in the raised position. This simplifies the automated treatment and processing of the containers during and after the treatment or processing of the containers but at the same time also prevents a collision of directly adjacent containers.

According to a further embodiment, the containers are received in the transport or packaging container such that the open end faces the bottom of the transport or packaging container. If the transport or packaging container is sealed, the containers are thus accommodated in the transport or packaging container in an upright position. The abovementioned positioning means may serve for a continued stabilization of the positions of the containers during the transport.

During the treatment or processing the containers are preferably arranged upright on the flat supporting base. Therefore, the transport or packaging container is placed on the supporting base or turned over it preferably from above after the treatment or processing of the containers. After the closing of the transport or packaging container, it can then be turned so that the containers are then disposed upside down in the transport or packaging container. The aforementioned positioning means on the bottom of the transport or packaging container may be formed for this purpose as receptacles for partially accommodating the containers or defining the positions of the containers in the transport or packaging container.

According to a further embodiment, at least one opening is formed in the flat supporting base or in the transport or packaging container through which a gas flows to sterilize the interior of the transport or packaging container. This respective opening can then be closed in a suitable gas-tight and/or sterile manner after sterilization. According to a further embodiment, this respective opening is covered with a gas permeable plastic foil, through which the gas used for sterilization can flow into the interior of the transport or packaging container.

According to a further embodiment the transport or packaging container is closed or sealed by a gas permeable plastic foil, in particular by a plastic foil, which is formed of a gas permeable fabric of synthetic fibers, and in particular by a Tyveck® foil. This gas-permeable plastic foil may also be used as the aforementioned flat supporting base. In order to avoid slippage of the containers on the plastic foil during the treatment or processing of the containers, suitable coatings for reducing friction may be provided on the underside of the containers or on the surface of the plastic foil, or adhesive points may be provided that are advantageously formed from an adhesive or bonding agent that does not outgas.

According to a further embodiment, respective adjacent supporting bases are directly coupled with each other for the treatment or processing such that they are immovable relative to one another in a longitudinal direction and/or in a transverse direction of the supporting base and that the directly adjacent supporting bases are passed together along the processing station or conveyed through it. The supporting bases can thus be concatenated to form larger units, which can simplify the handling and conveyance in a processing plant.

For this purpose positive-fit structures, which are formed correspondingly to each other may be formed on the rims of directly adjacent supporting bases, which are transferred into a positive-fit engagement with each other for the treatment or processing of the containers. The base areas of the recesses and/or projections, if respectively viewed in a plan view, may in particular differ from a rectangular shape and be formed directly corresponding with each other so that a positive-fit in the manner of a simple dovetail-joint can be implemented, which enables a particularly stable connection between adjacent supporting bases, which can be released easily again.

According to a further embodiment, the positive-fit structures comprise, at a first of the two adjacent supporting bases, a resilient tongue having a locking projection or a locking recess formed thereon and, at the second of the two adjacent supporting bases, a receptacle, which is formed correspondingly to the locking projection, or a protrusion, which is formed correspondingly to the locking recess, which are brought into the above-mentioned positive-fit engagement for connecting the adjacent supporting bases.

To reduce the base area of a flat supporting base, its rims may be formed as removable members or members that can be pivoted away, which are removed or pivoted away for the treatment or processing. This can further increase the throughput of process plants.

A further aspect of the present invention relates to a supporting base for concurrently supporting or guiding a plurality of containers serving for storage of substances for cosmetic, medical or pharmaceutical applications, or containing the same, in particular of flasks (vials), during the treatment or processing of the containers in a processing plant. According to the present invention this supporting base is formed as disclosed in the present application.

A further aspect of the present invention relates to the use of a flat supporting base as disclosed in the present application, which serves for closing or sealing a transport or packaging container, which has a bottom, a circumferential side wall and an insertion opening opposite to the bottom opposite or which is received in the closed or sealed transport or packaging container for transportation, as a supporting base for a plurality of containers used for storage of substances for cosmetic, medical or pharmaceutical applications, or containing the same, in particular of flasks (vials), during their treatment or processing at or in a processing station, wherein the plurality of containers are arranged in a predetermined arrangement on the flat supporting base such that the bottoms of the containers rest directly on the flat supporting base. According to the present invention this supporting base is formed as disclosed in the present application.

A further aspect of the present invention relates to a transport or packaging container for a plurality of containers for substances for cosmetic, medical or pharmaceutical applications, in particular of flasks (vials), particularly for use in the process as described above, wherein the containers are formed to be open at one end, wherein the transport or packaging container comprises a bottom, a circumferential side wall and an insertion opening opposite to the bottom, and wherein said insertion opening of said transport or packaging container is closed or sealed, comprising a plane supporting structure, which comprises a plurality of openings or receptacles, which are formed and arranged in a predetermined arrangement and into which the containers can be inserted for concurrently supporting the plurality of containers at said supporting structure, wherein the plane supporting structure together with the plurality of containers held thereon is accommodated in the closed or sealed transport or packaging container. According to the present invention the plane supporting structure is not formed integrally with the transport or packaging container, and the open ends of the containers respectively face the bottom of the transport or packaging container. According to the present invention the supporting base and the transport or packaging container are formed as disclosed in the present application.

OVERVIEW OF THE DRAWINGS

In the following the invention will be described in an exemplary manner and with reference to the accompanying drawings, from which further features, advantages and problems to be solved will become apparent. In the drawings:

FIGS. 2a-2b show in an exploded perspective view and in a partial section a transport or packaging container and a flat supporting base according to a first embodiment of the present invention;

FIG. 2e shows the transport or packaging container according to FIG. 2d in a schematic plan view onto a bottom thereof;

FIGS. 4a-4b show in a perspective plan view and a top view a transport or packaging container according to a further embodiment of the present invention;

FIG. 4c is a perspective plan view and a partial section of a transport or packaging container according to another embodiment of the present invention;

FIGS. 4d-4e are a perspective plan view and a longitudinal section of a transport or packaging container according to a further embodiment of the present invention;

FIG. 7d shows in a greatly enlarged partial plan view the connection between two flat supporting bases or supporting structures according to a further embodiment; and FIG. 7e is a cross section taken along A-A according to FIG. 7d.

In the drawings, identical reference numerals designate identical or substantially equivalent elements or groups of elements.

DETAILED DESCRIPTION OF PREFERRED EMBODIMENTS

Figure 3A:
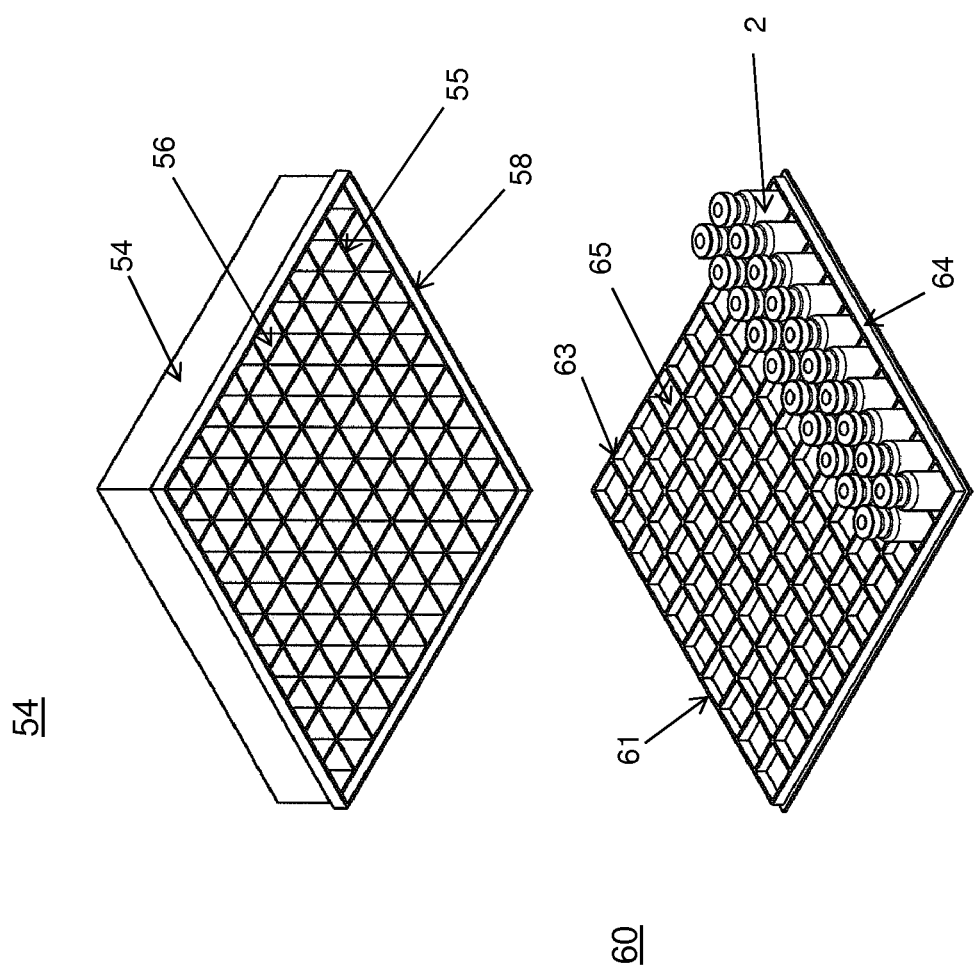
FIGS. 3a-3b show in an exploded perspective view and in a partial section a transport or packaging container and a flat supporting base according to a third embodiment of the present invention.
Figure 3B:
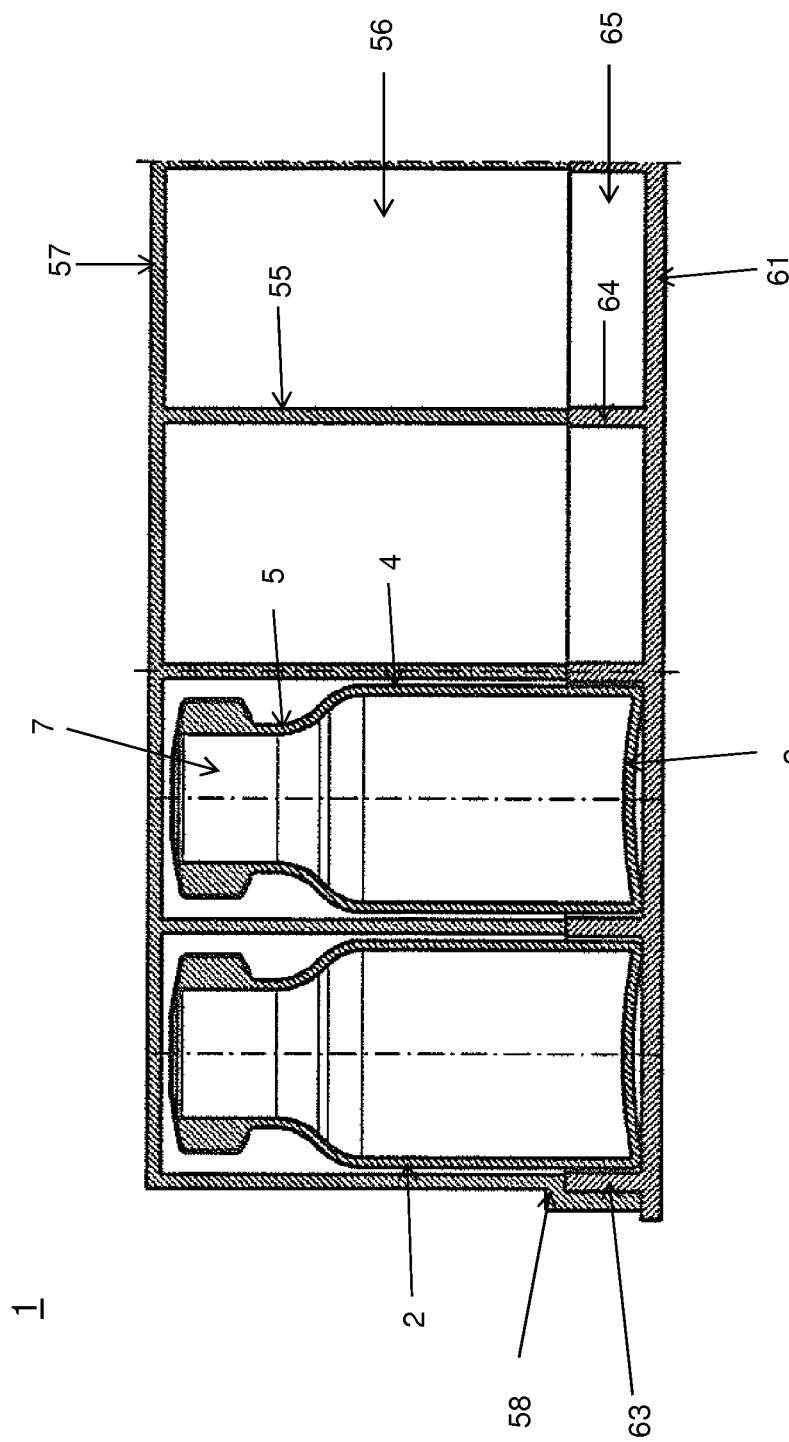

An example of medication containers in accordance with the present application embodied as vials is schematically shown in FIG. 3b in a longitudinal section. These have a cylindrical basic shape, with a cylindrical side wall 4 with—within tolerances—constant inside and outside diameters projecting vertically from a flat bottle bottom 3, which merges in a constricted neck portion 5 of a relatively short axial length near the upper open end 7 of the vial 2 and then merges in a widened upper rim (seam) 6 (also rolled rim), which has a larger outer diameter than the associated neck portion 5 and is configured for connection to a closure member. As can be seen from FIG. 3b, the bottom side of the rolled rim 6 is slanted and extends downward at an acute angle toward the constricted neck portion 5. Although in FIG. 3b it is shown that the bottom 3 is formed slightly inwardly bulged, it may be preferable that the bottom 3 is formed flat, in particular in order to ensure a full-surface contact as possible to a supporting or cooling surface on which the vial rests.

The neck portion 5 can be formed with smooth walls and without an external thread or may be provided with an external thread for screwing on a closure member. For example, a plug (not shown) may be inserted in the inner bore of the neck portion 5 and the upper rim 6, whose upper end is connected with the upper rim 6 of the vial in a gas-tight manner and protected against the intrusion of contaminants into the vial, for example by crimping or beading a metal protective foil which is not shown. Such vials are radially symmetrical and made of a transparent or colored glass or by blow molding or plastic injection molding techniques of a suitable plastic material, and can be in principal internally coated so that the material of the vial emits minimal impurities to the agent to be received.

Another example of a container according to the present application are ampoules, carpoules, syringes or injection containers. Ampoules or carpoules are containers for medication agents for usually parenteral administration (injection), for cosmetics and other agents and are usually cylindrical in shape with an extended tip (spear or head) and a flat bottom or also with two extended tips at both ends. These may be formed in particular as snap-off ampoules with an annular predetermined breaking point around the ampoule neck or as an OPC cartridge (One-Point-cut ampoule) having a breaking ring inscribed into the glass. Syringes or injection containers, also known as injection flask, vial or reusable ampoule, are cylindrical containers of glass or plastic shaped similar to a bottle, usually having a relatively small nominal volume (e.g. 1 ml, 10 ml). They are sealed with a rubber plug with septum (puncture rubber). For protecting the septum and fixing the rubber plug an outer closure (beaded cap or cramp), often made from an aluminum sheet, is necessary. In a carpoule the liquid is stored in a cylinder, which is closed at one end by means of a thick rubber or plastic plug. This acts as a piston when the content is pressed out using a carpoule syringe. At the other end the cylinder is closed only by means of a thin diaphragm, which is pierced from the rear end of the carpoule syringe (a cannula sharpened on both sides) in the application. Cylindrical ampoules are often used in dentistry for local anesthesia. Special cylindrical ampoules with a specially shaped front part (e.g. thread) are used for insulin therapy in insulin pens.

According to the present invention, such containers are used for storage of substances or agents for cosmetic, medical or pharmaceutical applications, which are to be stored in one or several components in solid or liquid form in the container. Especially in the case of glass containers storage periods can amount many years, notably depending on the hydrolytic resistance of the glass type used. While, in the following, cylindrical containers are disclosed, it should be noted that the container, in the sense of the present invention, may also have a different profile, for example a square, rectangular or polygonal profile. Inevitably such containers have tolerances due to the production which can be of the order of one or several tenths of a millimeter in particular for glass containers.

Referring to FIG. 2a, a flat supporting base 60 (which is often named as a so-called "nest" in the prior art) serving as a supporting structure is formed on a base plate 61 by transverse webs 64 crossing each other at right angles. In this manner, elongate, cylindrical receptacles 65 for receiving the containers 2 are formed, wherein the bottoms of the containers 2 directly rest on the base plate 61. The base plate 61 may be made of a material having an excellent thermal conductivity, in particular of a metal or a plastic material having a high thermal conductivity, into which metal particles may be incorporated to increase its thermal conductivity. The upper part of FIG. 2a shows a transport or packaging container 10 having a circumferential side wall 12, 14 and a top rim 15 and will be described in more detail below with reference to FIG. 4a. On the bottom of the transport or packaging container 10 a structure of rectangular crossing transverse webs 55 is formed or disposed to form a plurality of elongated and cylindrical cavities 56 having an opening width that is preferably larger than the opening width of the associated elongated receptacle 65 on the base plate 61 and the maximum outer dimension of the container 2 in a given engagement area, respectively. The transverse webs 55 on the bottom of the transport or packaging container 10 and the transverse webs 65 of the flat supporting base 60 are intended only to serve to prevent the side walls 4 of the container 2 directly contact each other, for example due to vibrations. In this way, damages to the side walls 4 of the containers 2 can be further prevented.

Referring to FIGS. 2a and 2b, the side walls 63 of the flat supporting base 61 are surrounded by a peripheral web 62, which, when the transport or packaging container 10 is placed on the base plate 61, then rests on the upper flange-like rim 15 of the transport or packaging container 10, as shown in the sectional view of FIG. 2b. When the transport or packaging container 10 is placed on the base plate 61 and the rim 15 and the peripheral web 62 are each sealed, for example by adhesive bonding or sealing hermetically from the surrounding area, a hermetically sealed packaging unit 1 is formed, which can be opened again by removal of the transport or packaging container 10 from the base plate 61. The semi-circular openings 66 in the rim 62 of the base plate can serve for a positioning or for a better gripping of a flat supporting base 60 or a concatenation of adjacent supporting bases 60.

In general, the containers 2 can be loosely received in the receptacles 65 of the flat supporting base 60. According to further embodiments, the containers 2 can also be frictionally or positively received in the receptacles 65 of the flat supporting base 60. According to FIG. 2b spacers 59 are disposed on the bottom 11 of the transport or packaging container 10, between which openings are formed through which a gas can flow, for example, for sterilization via the filling openings 7 into the interior volume of the containers 2. Usually, the transport or packaging container 10 would be transported together with the base plate 61 downward, so that the containers 2 can be kept and transported with the head pointing down.

Figure 2D:
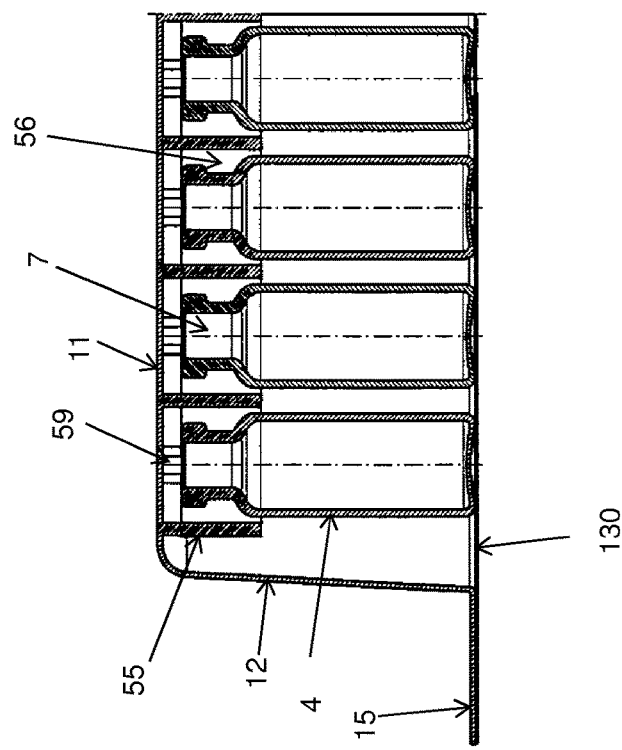
FIGS. 2c-2d show in an exploded perspective view and in a partial section a transport or packaging container and a flat supporting base according to a second embodiment of the present invention.
Figure 2C:
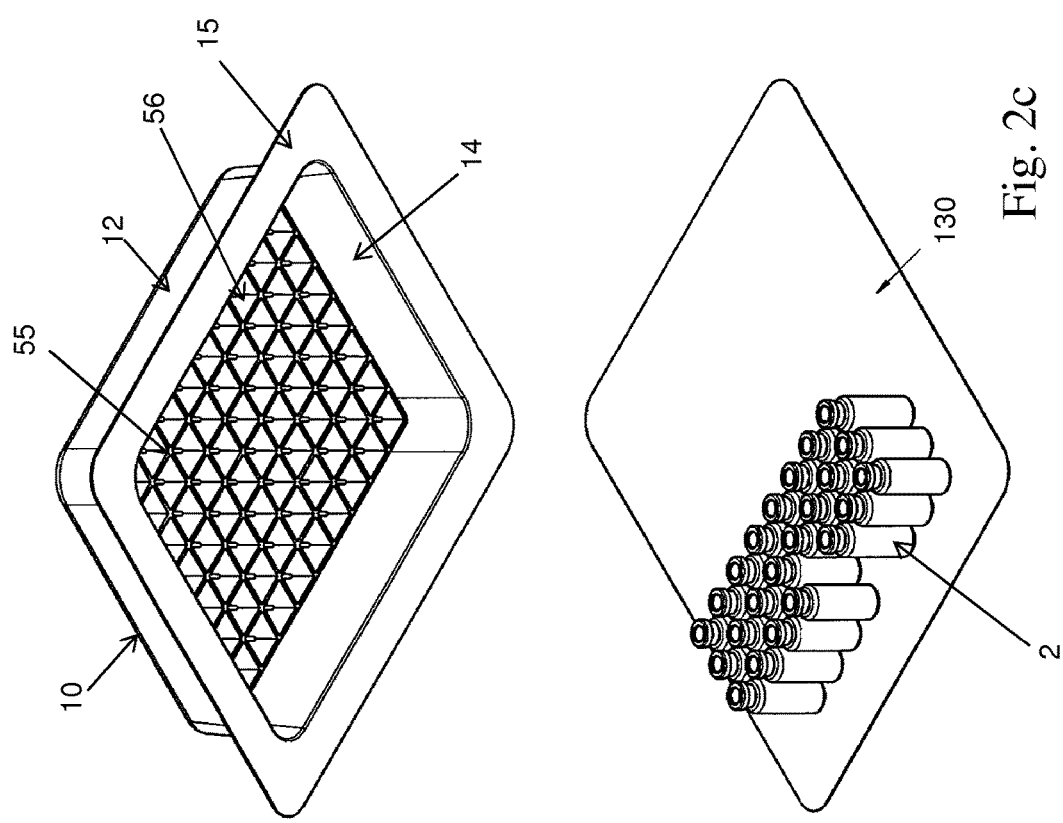

In a further embodiment according to FIG. 2c, the containers 2 are located directly on a protective or wrapping foil 130 on which a transport or packaging container 10 (often also named a so-called "tub" in the prior art) is placed, wherein the transverse webs 55, which are disposed on the bottom of the transport or packaging container 10, prevent a direct contact between the side walls 4 of the containers. At their upper end the containers may also be fixed by friction by the transverse webs 55, in particular they may be clamped. The foil 130 may in particular be a sterile but gas-permeable foil, in particular a plastic mesh, such as Tyveck®. Alternatively, the flat supporting base 130 can be made of a thin metal sheet or a thin plastic plate. Preferred are materials with an as high as possible thermal conductivity, as described below.

In this embodiment the containers received in the transport or packaging container 10 can be sterilized by blowing a gas through the foil 130. In order that the inflowing gas can flow into the interior of the containers 2, spacers 59 are provided between the bottom 11 of the transport or packaging container 10 and the upper rim of the containers 2, as described above with reference to FIG. 2b, so that the containers 2 do not directly rest on the bottom 11.

FIG. 2d shows a top view onto the insert formed on the bottom of the transport or packaging container 10, which may also be removable. The spacers 59 may extend in diagonal direction from the corners of a respective receptacle 56 to the center of the respective receptacle 56. The cross-shaped spacer webs 59, however, are not connected to each other so that the upper rim of the containers is freely accessible in the region of the center of a respective receptacle 56. FIG. 2d shows a top view onto the insert formed on the bottom of the transport or packaging container 10, which may also be removable.

FIG. 3a shows a further variant of a flat supporting base 60, wherein the afore-mentioned rim portion 62 of the base plate 61 (see FIG. 2a) is very narrow, so that the side walls 63 of the supporting structure 60 are received directly in the correspondingly shaped rim portion 58 of the insert 54, as shown in the sectional view of FIG. 3b. In the assembled state as shown in FIG. 3b, a transportation and packaging unit 1 is also formed, which can be hermetically sealed against the external environment. Referring to FIG. 3b, the bottoms 3 of the containers are directly supported on the base plate 61. Near their lower ends, the containers 2 may be received generally loosely in the elongated receptacles 65 formed by the transverse webs, i.e. with a certain radial play, or they can be fixed frictionally or positively in a suitable manner.

Although in the foregoing it has been described, that the flat supporting base closes and seals the transport or packaging container, in the following and with reference to FIGS. 4a to 4c further embodiments will be described according to which the flat supporting base is a separate element, which is inserted into the transport or packaging container after the treatment or processing of the containers together with these containers before the transport or packaging container is closed or sealed.

In the illustrated embodiment according to FIG. 4a, the supporting base 25 is formed as a separate insert having a plurality of transverse webs 35, which intersect each other perpendicularly, forming a plurality of elongate or cylindrical receptacles 39 having a square cross-section, wherein the receptacles 39 in a are arranged matrix arrangement. Here, the containers 2 are received in the receptacles 39 either loosely or with a radial clearance or they are held frictionally or positive-fit by the transverse webs 35 or by holding means provided in this area, so that the bottoms of the containers 2 directly rest on the bottom 40 of the supporting base 25. In this way, also in this embodiment a good thermal contact between the bottoms of the containers and a cooling plane is ensured. Basically the supporting base or insert 25 may also be formed integrally with the bottom 11 of the transport or packaging container 1. FIG. 4b shows the transport or packaging container 1 according to FIG. 4a in a schematic plan view.

Referring to F. 4a, the transport or packaging container 10 is substantially box- or trough-shaped and has a base 11, a circumferential side wall 12 extending perpendicular from the base 11, a step 13 projecting substantially perpendicular from the side wall 12, a circumferential upper side wall 14 and an upper rim 15, which is formed like a flange. The corners 16 of the container 10 are suitably rounded. The upper side wall 14 may be formed inclined at a small angle of inclination to the vertical on the bottom 11 in order to facilitate the insertion of the supporting structure 25. Such a container 10 is preferably formed from a plastic material, particularly by plastic molding, and is preferably formed of a clear transparent plastic, to enable an optical visual inspection of the received support structure 25 in the container 10, and held by the container 2.

Although in FIG. 4a, the bottom 11 of the illustrated transport or packaging container 10 is shown to be closed and formed integrally with the side wall 12, the lower end of the transport or packaging container 10 may also be formed 10 opened in the manner of the upper end, in particular it may be provided with a flange-like bottom rim in the form of the upper edge 15 so that the bottoms of the containers are accessible from the underside of the transport or packaging container 10, here, for example, for processing steps in a sterile tunnel or in a freeze-dryer.

According to further embodiments, in the bottom 11 or the sidewall 12 at least one opening (not shown) may be formed, through which a gas can flow for sterilizing the interior volume of the transport or packaging container 10. Such an opening is closed, for example, with a sterile plastic foil, as described above with reference to FIG. 2c.

FIG. 4c shows a further variant, in which the supporting base 25 is formed as an insert, in which a plurality of cylindrical receptacles 39 are formed, which are formed by circumferential sidewalls 35. Deviating from FIG. 4a according to FIG. 4c the insert 25 is supported on the step 13 of the transport or packaging container 10. Also in this embodiment the bottoms of the containers 2 directly rest on the bottoms of the receptacles 39 in order to ensure a good thermal contact with a supporting surface.

According to the variant of FIGS. 4d and 4e such a supporting base 25 may also be used directly as transport or packaging container 1. To this end, the open ends of the receptacles 39 are closed by means of a sterile packaging foil 130, in particular a sterile but gas-permeable plastic foil, as described above with reference to FIG. 2c, which is glued or sealed on the upper rim of the insert 25. The protective foil 130 may be, in particular, a gas-permeable plastic foil, in particular a meshwork of synthetic fibers, such as polypropylene fibers (PP), or a Tyvek® protective foil, which enables sterilizing of the containers 2 received and packaged in the supporting structure 25 by the foil 130.

Figure 5:
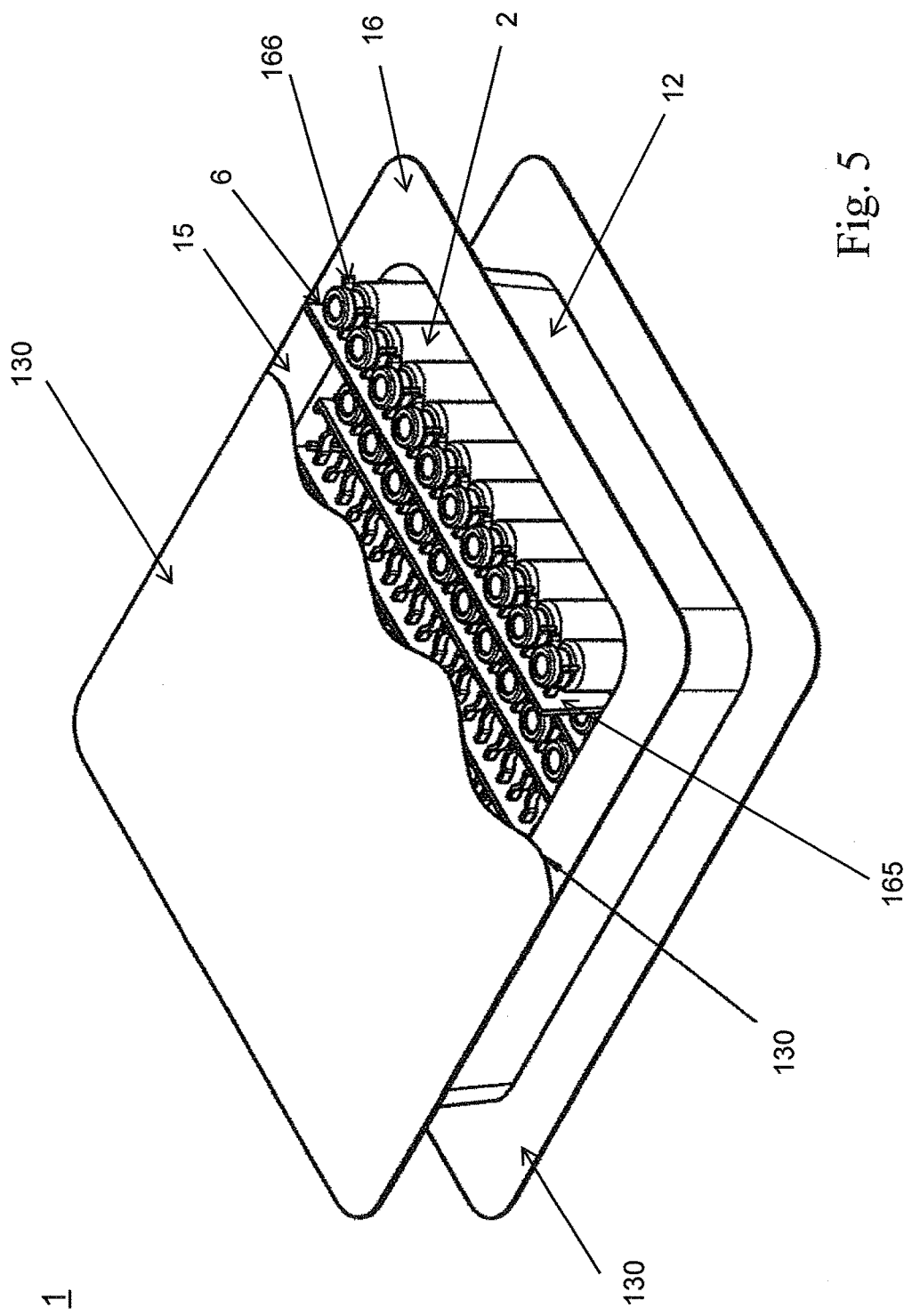
FIG. 5 is a perspective plan view and a partial section of a transport or packaging container according to a further embodiment of the present invention.

According to the variant of FIG. 5 both ends of the transport or packaging container are designed to be open and these are sealed by a sterile packaging foil as described above or by a plate or closed. According to FIG. 5, the flat supporting base is formed as a box having circumferential side walls 12. This box is divided into a plurality of rectangular segments by a plurality of transverse webs 165, which are parallel with each other and which are mutually spaced apart one another at regular intervals transverse webs 165 is. These cross-bars can be mounted in the box.

Supporting arms are arranged on the surfaces of the transverse webs 165 at the same height and at regular distances from each other concavely curved, which are formed from an elastic plastic and are either formed integrally with the transverse webs 165 or secured to them or are integrally formed. The supporting arms 166 form receptacles, into which the containers 2 can be inserted from the front so that their neck portions may be positively embraced and the upper rim may be supported thereon. Viewed in the longitudinal direction of the containers 2, a positive fit or friction fit exists. However, by applying a suitable axial force, the containers 2 can slide axially in the receptacles formed by the supporting arms 166, for example, to a raised position. The transverse webs 165 are positioned or suspended in the box in such a manner, that the bottoms of all containers 2 are flush with the bottom rim of the box, so that a direct contact between the bottoms of all containers 2 and the can be ensured when the box is placed on that supporting or cooling surface. Together with the plastic foil 130 applied to the top and bottom rim, a transport or packaging container 1 is also formed in which the plurality of containers 2 are packed in a sterile and safe manner and can be transported.

Figure 1A:
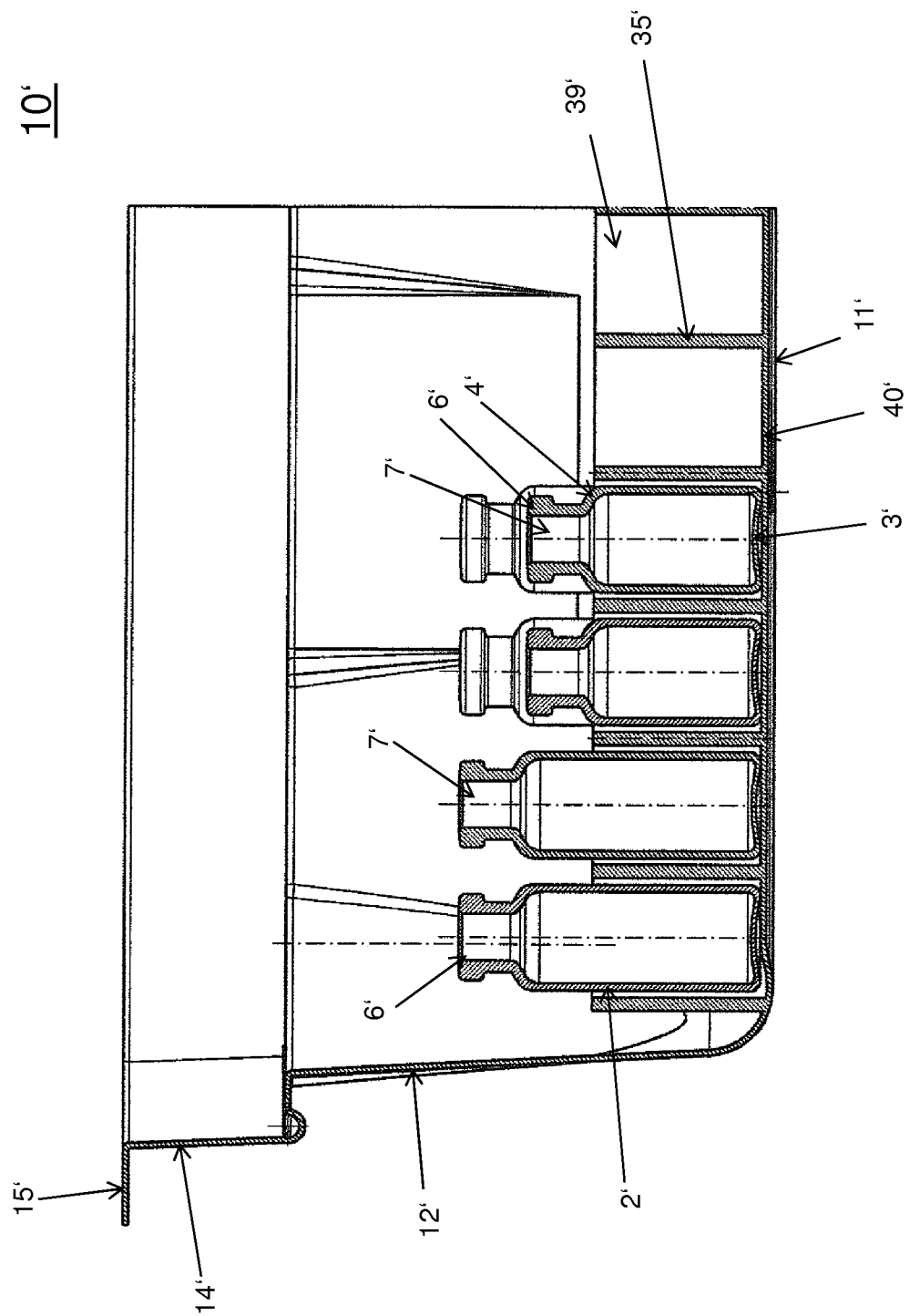
FIG. 1a is a transport or packaging container according to the prior art.
Figure 1B:
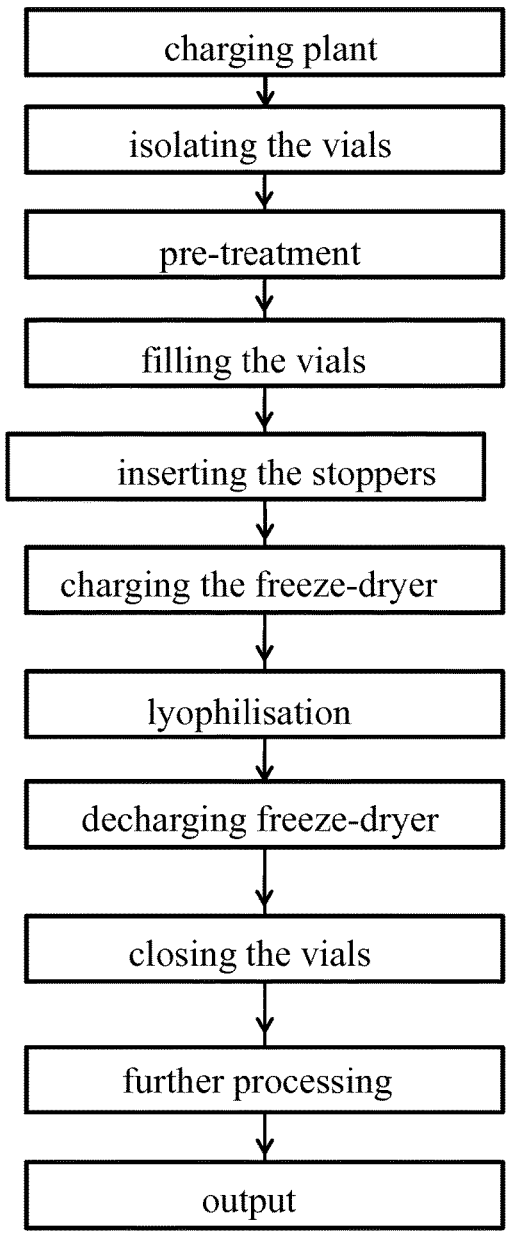
FIG. 1b is a flow chart of a conventional process for the treatment or processing of containers.
Figure 6A:
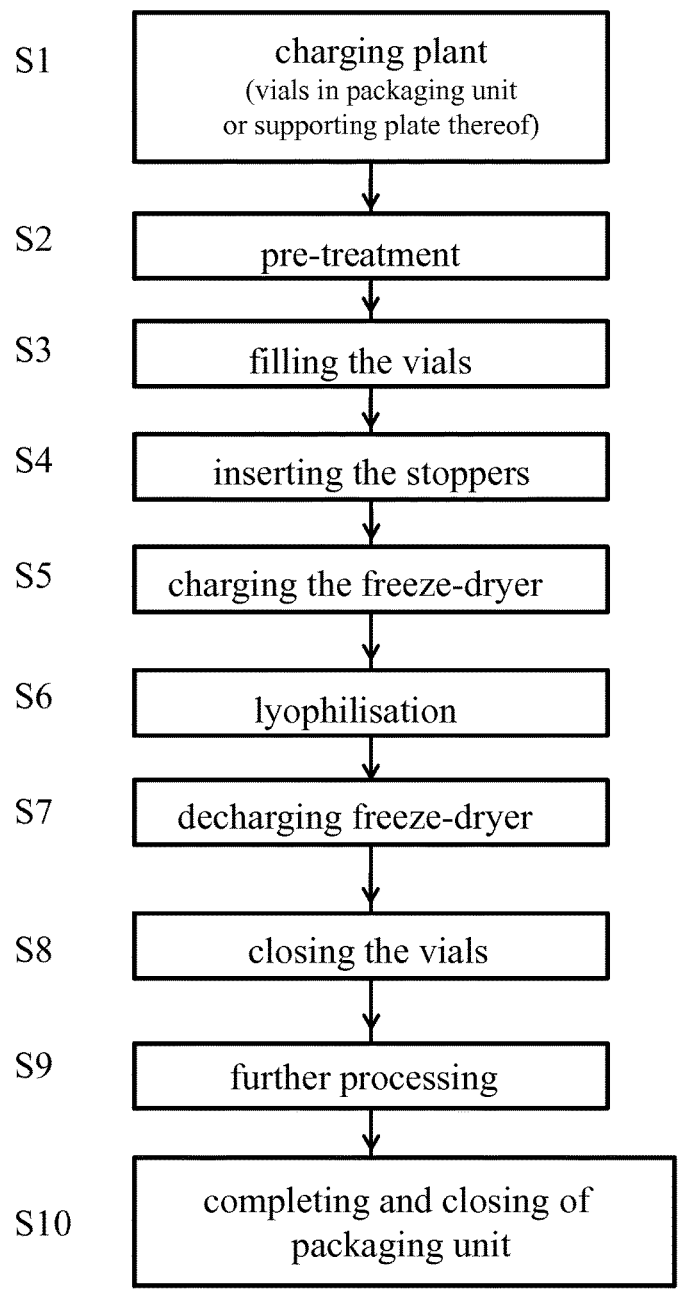
FIG. 6a is a flowchart of a process for treatment or processing of containers according to the present invention.

FIG. 6a shows a schematic flow diagram of a process step for treatment or processing containers, namely, as an example a freeze-drying process, wherein, in contrast to a conventional process step, as described above with reference to FIG. 1b, a plurality of containers together can be held or at least received at/by a flat supporting base in the process steps S1 to S9, in any event in the process steps S5 to S7, so that the bottoms of the containers rest directly on the bottom of the flat supporting base, as described above.

Firstly, the processing plant, for example a sterile tunnel, is charged in step S1. For this purpose, the vials are placed on flat supporting bases as described above. Usually the vials stand upright on the supporting bases, i.e. with their filling opening directed upward. In other embodiments, in which the receptacles of the supporting base are configured such that the vials can be held with a certain retaining force, it is, in principle, also possible that the vials are held vertically downward below the supporting base. In any case it is ensured that the bottoms of the vials rest directly on the bottom of the supporting base. In step S1, supporting bases charged in such a manner are conveyed into the processing plant by a conveyor, for example a transport belt. In step S2 a pretreatment is performed optionally, such as a washing and sterilization of the vials. Subsequently, the vials are filled in step S3 and optionally suitable plugs that are still open are placed in step S4.

Figure 6B:
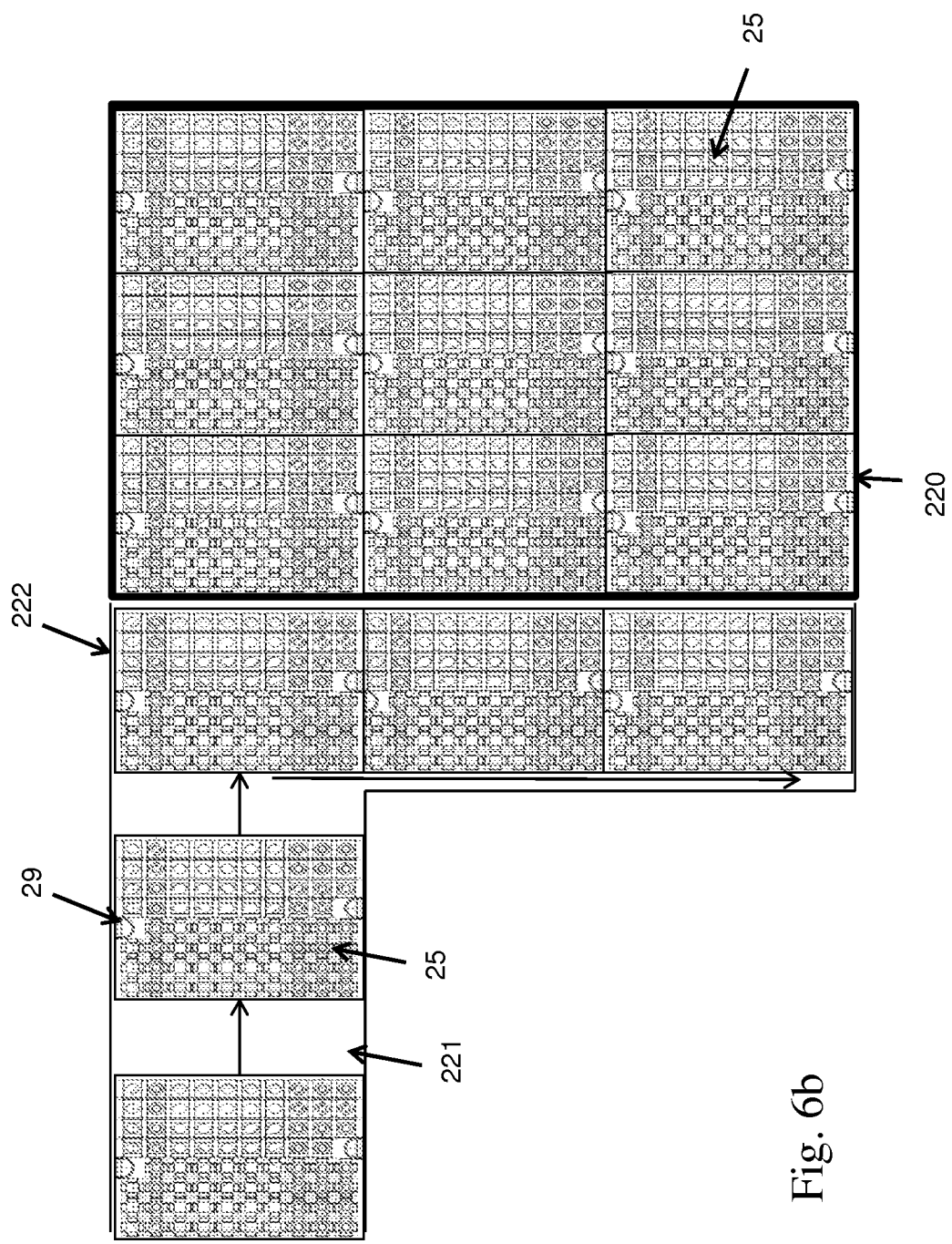
FIG. 6b shows in a schematic plan view the application of a process according to the present invention for freeze-drying an agent in the containers.

Then the freeze-dryer is charged in step S5. This is schematically shown in the plan view of FIG. 6b. The flat supporting bases 25 with the containers held by it in a regular two-dimensional array are conveyed by means of a conveying device 221, for example a conveyor belt or a roller track, in the direction of the arrow towards a freeze-dryer 220. This may for example be arranged laterally to a main conveyor of a processing plant, not shown, from which the supporting bases 25 can be transferred or deflected onto the conveyor 221 and conveyed towards the freeze-dryer 220. In front of the freeze-dryer 220 a supporting surface is provided, which extends transverse to the conveyor 222, on which the supporting bases 25 can be collected. This collection of the supporting bases 25 in front of the freeze-dryer 220 can also be performed on several levels, in correspondence to the levels of the freeze-dryer 220.

The flat supporting bases 25 with the containers arranged on it, are charged into the freeze-dryer 220 for freeze-drying and directly rest on a cooling surface or on a cooling finger of the freeze-dryer 220 during the freeze-drying process. As the bottoms of the containers in turn directly rest on the bottom of the flat supporting base 25, a good thermal contact with the cooling surface or the cooling finger of the freeze-dryer 220 is ensured. For this purpose it is preferred that the flat supporting base 25 is made of material having a high thermal conductivity (for example, of a metal, metal foam, metal composite, metal composite foam or a plastic material having a high thermal conductivity, in which in particular metal particles are embedded) and/or that it is formed with a material thickness as low as possible. The flat supporting base 25 may also be formed of a fiber reinforced plastic or of a plastic material, to which ceramics or metals are added to increase its thermal conductivity. As it is known, fiber-reinforced plastics have a higher thermal conductivity of up to 0.9 W/(m K) as carbon fibers. If ceramics or metals are added to the plastic materials, the thermal conductivity is further enhanced. So-called heat-conductive plastics are formed. Thus, a thermal conductivity of 20 W/(m K) is accomplished.

After unchargeing the freeze-dryer 220 in step S7, the vials are closed, in particular by beading or crimping a metal cap on the upper rims of the vials (step S8). After an optional further processing (Step S9), finally the flat supporting bases are inserted into a transport or packaging container (the embodiment according to FIG. 4a or FIG. 4c), which is subsequently closed or sealed. Or the supporting bases are directly used for closing (embodiment of FIG. 2a or FIG. 3a) or sealing a transport or packaging container (embodiment of FIG. 2c).

In order that the above-described flat supporting bases can also be used for other process steps without the necessity of removing the vials from the supporting base, further features may be provided, which will be described in the following with reference to FIGS. 7a to 7e. As an example, it may be required that the vials need to be raised to a raised position during a process step, in which they no longer rest directly on the bottom of the flat supporting base. For this purpose it is preferred that a lifting device, for example a vertically movable rod, may act from the bottom side on the vials because the intrusion of contaminants due to mechanical abrasion and the like into the internal volume of the vials can then be prevented. For this purpose, according to FIG. 7a holes 68 may be provided in the bottom 60 of a flat supporting base, not shown, in more detail, for example in the center of a respective receptacle 65 (see FIGS. 2a and 3a). The opening width of the opening 68 on the one hand is of such a dimension that the bottom 3 of the vial cannot slide through so that the base 3 can be supported on the bottom 60, and on the other hand, of such a dimension that the lifting device, e.g. in the example of FIG. 7a the vertically movable rod 240, with its supporting surface 246 provided at the front end thereof can pass through the opening 68. Particularly for freeze-drying applications, it is of course preferred that the opening width of the opening 68 is as small as possible in order to ensure the best possible thermal contact as mentioned above. By raising the rod 240, the vial resting on the supporting surface 246 can be lifted. For depositing the vial on the bottom 60 of the flat supporting base (not shown) the rod 240 together with the bearing surface 246 provided thereon is drawn back down through the opening 68.

Figure 7A:
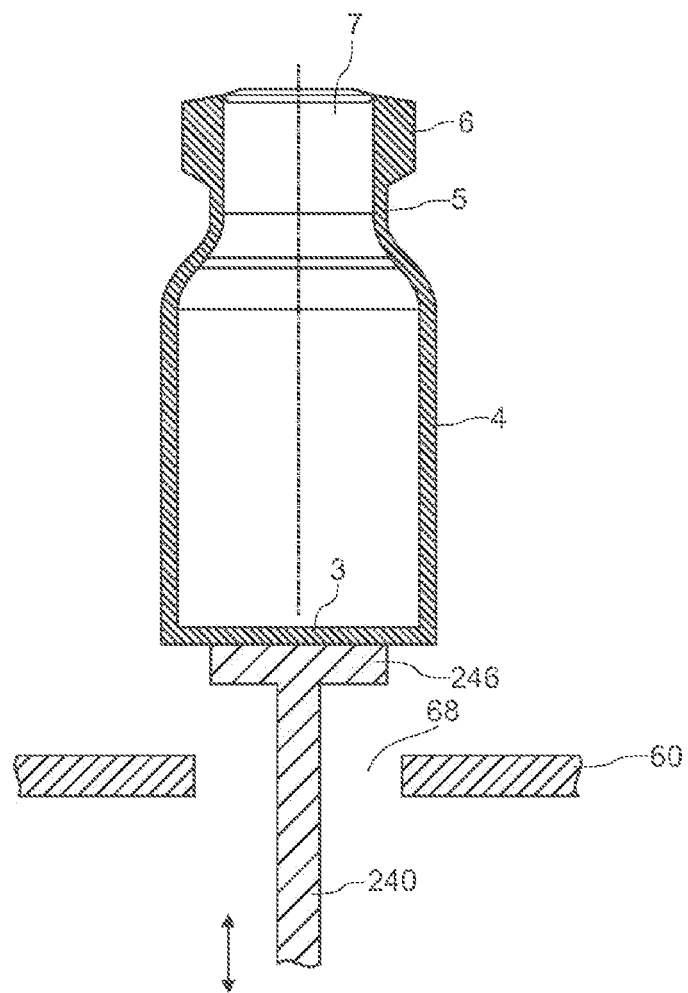
FIG. 7a shows a process step of the process according to the present invention, wherein a container is transferred to a raised position by means of a lifting device for further treatment or processing, which extends through an opening of a flat supporting base or of the transport or packaging container.
Figure 7B:
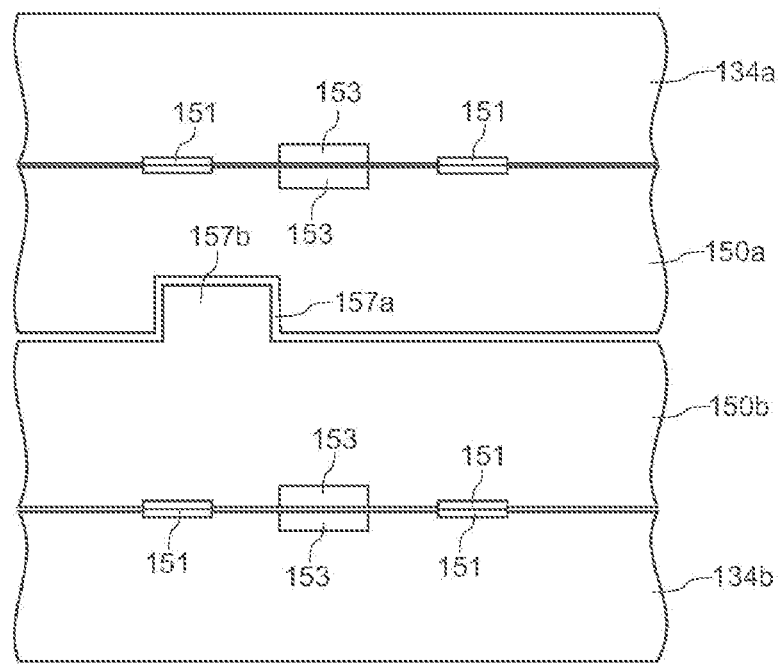
FIG. 7b shows a variant of a flat supporting base or a supporting structure of the present invention, having projections and recesses on the removable or retractable members that serve to further increase the packing density.
Figure 7C:
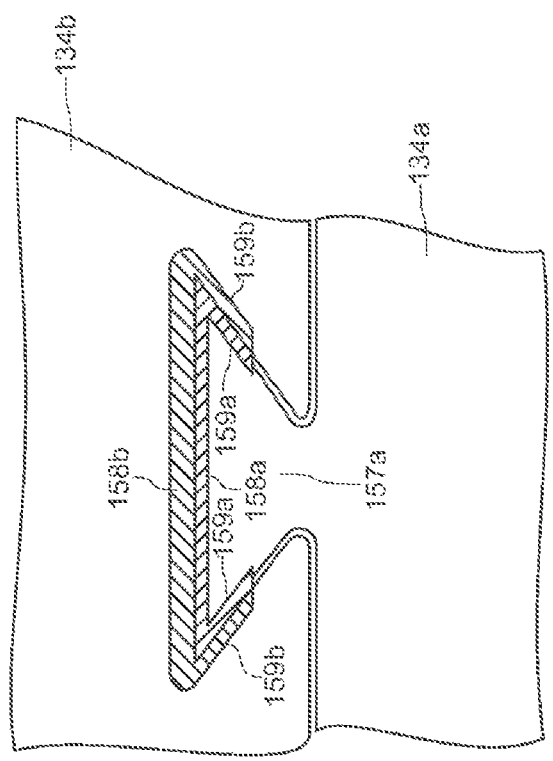
FIG. 7c shows in a schematic plan view another variant of the projections or recesses according to FIG. 7b.

FIG. 7b shows in a greatly enlarged partial cross-sectional and plan view of further variant of a flat supporting base 134a, 134b (only partially shown), whose rims 150a, 150b can be flapped away to further reduce the base area of the respective supporting base, for example, if this together with the vials is to be transferred to a cramped processing station, such as a freeze-dryer with limited base area. For this purpose, the rims 150a, 150b are connected to the respective supporting base via hinges 151. Particularly, the hinges 151 may be formed as film hinges or snap-spring hinges and may be formed integrally with the supporting base 134 of a plastic material.

According to FIG. 7b recesses 157a and/or projections 157b are formed at the removable or pivotal members 150a, 150b. The recesses 157a and/or projections 157b of the removable or pivotal members 150 of a supporting base are formed correspondingly to the recesses 157a and/or projections 157b of the removable or pivotal members 150 of an directly adjacent flat supporting base so that a positive fit between these recesses 157a and/or protrusions 157b can be formed for defining and stabilizing the mutual position of the supporting bases.

On the upper side of the supporting bases 134a, 134b and the rims 150a, 150b, block-shaped stops 153 are provided at corresponding positions defining, by mutual abutment, a coplanar alignment of the rims 150a, 150b and the supporting base 134 and preventing a folding-up of the rims 150a, 150b. The supporting bases can therefore also be supported by the rims in a transport or packaging container.

According to a further embodiment (not shown), the rims 150 may also be removed from the supporting base 134. The rims 150 may of course be provided along all four longitudinal sides of the supporting base 134.

The above projections 157b and recesses 157a may also be formed directly on the rim of a flat supporting base.

Due to the afore-mentioned design of the protrusions 157b and recesses 157a, two flat supporting bases can generally also be latched together, so that these cannot be moved relatively to each other in a longitudinal direction and/or in a transverse direction of the supporting base and so that directly adjacent supporting bases are together conveyed along a processing station or can pass through them.

An example for the configuration of the projections and recesses 157a, 157b for achieving a latching in the form of a dovetail-joint is exemplified in the greatly enlarged partial plan view according to FIG. 3c. The projections 157b and recesses 157a each have, if viewed in a plan view, an overall triangular or polygonal base and are formed correspondingly to each other, so they can be latched directly to one another. At least partially along the edges of the projections 157a and recesses 157b side walls 158, 159 are formed which protrude perpendicularly from the surface of the support base 134. These side walls 158, 159 follow the contour of the associated recess 157a and of the associated projection 157b, respectively, and act as a stop and guide surface preventing that the supporting bases are slid or moved one above the other in a stacked manner. In the latched state according to FIG. 7c, the side walls 158a of the lower supporting plate 134a directly abut to the side walls 158b of the upper supporting plate 134b. Furthermore, the angled side walls 159b of the upper supporting plate 134b are located immediately adjacent to the angled side walls 159a of the lower supporting plate 134a.

FIG. 7d shows a further example of a positive-fit connection in a greatly enlarged partial plan view, namely the connection of two supporting bases 134a, 134b according to a further embodiment. According to FIG. 7d a resilient tongue 148 protrudes perpendicularly from the projections 157b, which have a rectangular shape here, of the lower supporting base 134a toward the associated recess of the upper supporting base 134b. As can be concluded from the schematic partial section of FIG. 7e along the line A-A of FIG. 7d, the resilient tongue protrudes from the plane defined by the supporting bases 134a, 134b, but extends parallel thereto. At the front end of the resilient tongue 148, a spherical projection 149a is formed, which engages in a correspondingly shaped receptacle on the upper surface 149b of the upper supporting base 134b. The supporting bases 134a, 134b can be pushed towards one another to be connected with each other, until the front end of the resilient tongue 148 with the projection 149a finally comes into contact with the upper surface of the upper supporting base 134b. When the two supporting bases 134a, 134b further approach each other, finally the resilient tongue 148 is bent upwards so that the protrusion 149a slides along the surface of the upper supporting base 134b, until it finally enters the region of the receptacle 149b and is pressed into the latter due to the restoring force of the resilient tongue 148. The elasticity of the tongues 148 and the configuration of the interlocking structures 149a, 149b define the strength of the releasable connection between the two supporting bases 134a, 134b in a simple manner. To prevent sliding of the two supporting bases 134a, 134b, also according to this embodiment, stop and guide surfaces may be provided, in particular embodied as side walls projecting perpendicularly from the upper surface of the supporting bases 134a, 134b, as described above with reference to FIG. 7c. In the embodiment of FIG. 7d such side walls would have to be provided in particular at the sides of the resilient tongues 148.

It will be readily apparent for the person skilled in the art upon reading the above description that the various aspects and features of the embodiments described above may be combined in any manner with one another, resulting in numerous further embodiments and modifications. It will be readily apparent for the person skilled in the art upon reading the above description that all such further embodiments and modifications shall be comprised by the present invention, as long as these do not depart from the general solution and scope of the present invention, as defined in the appended claims.

What is claimed is:

1. A process for treatment or processing of a plurality of containers used for cosmetic, medical, or pharmaceutical applications, each container of the plurality of containers having an open upper end and a closed bottom end at an opposite end thereof, the plurality of containers being accommodated in a sealed transport or packaging container, the sealed transport or packaging container comprising:
   a flat supporting base, and
   a box-shaped transport or packaging container having a bottom, a circumferential side wall, and an insertion opening opposite to the closed bottom, wherein
   the plurality of containers are disposed in a predetermined arrangement on the flat supporting base so that the closed bottom ends of the plurality of containers rest directly on the flat supporting base, and
   the box-shaped transport or packaging container is positioned upside down with the inserting opening on the flat supporting base to provide the sealed transport or packaging container accommodating the plurality of containers,
   the process comprising:
   opening the sealed transport or packaging container accommodating the plurality of containers by removing the box-shaped transport or packaging container so that the open upper ends of the plurality of containers supported on the flat supporting base are exposed;
   conveying the plurality of containers, while resting with the closed bottom ends directly on the flat supporting base, past a processing station or through the processing station by a conveying device for treatment or processing of the plurality of containers at the processing station or in the processing station without requiring the plurality of containers to be turned over; and
   putting the box-shaped transport or packaging container upside down with the inserting opening on the flat supporting base after the treatment or processing of the plurality of containers to provide the sealed transport or packaging container in which the plurality of processed or treated containers supported on the flat supporting base are accommodated.

2. The process of claim 1, wherein the sealed transport or packaging container seals the plurality of containers sterile against the environment.

3. The process of claim 1, wherein positioning devices are formed on the bottom of the flat supporting base or of the box-shaped transport or packaging container, which cooperate with the plurality of containers, so as to define the predetermined arrangement of the plurality of containers.

4. The process of claim 3, wherein the positioning devices prevent a collision of directly adjacent containers while the plurality of containers are resting on the flat supporting base or are accommodated in the sealed transport or packaging container.

5. The process of claim 3, wherein the positioning devices are formed as cylindrical or polygonal receptacles and the plurality of containers are at least partially inserted into the receptacles.

6. The process of claim 3, further comprising openings formed between the positioning devices through which a lifting device extends to, wherein
   the lifting device raises the plurality of containers to a raised position for treatment or processing in the processing station or at the processing station, in which the closed bottom ends of the plurality of containers do not directly rest on the flat supporting base.

7. The process of claim 6, wherein the plurality of containers continue cooperating with the positioning devices in the raised position, so that the predetermined arrangement is still defined by the positioning devices in the raised position.

8. The process of claim 1, further comprising an opening formed in the flat supporting base or an opening in the box-shaped transport or packaging container allows gas flow therethrough for sterilization of the interior of the sealed transport or packaging container.

9. The process of claim 1, wherein the flat supporting base is made of a metal, a metal-containing material or a plastic material having a high thermal conductivity.

10. The process of claim 9, wherein the flat supporting base consists of a plastic material having metal particles embedded therein to effect the high thermal conductivity.

11. The process of claim 1, wherein the processing station is a freeze-dryer, in which a lyophilization process is performed, wherein
   the closed bottom ends of the plurality of containers rest directly on the flat supporting base during the lyophilization process, and
   the flat supporting base rests directly on a cooling surface of the freeze-dryer.

12. The process of claim 1, wherein the flat supporting base is a gas permeable plastic foil, the plastic foil being formed of a gas permeable fabric of synthetic fibers.

13. The process of claim 1, wherein
   respectively adjacent supporting bases are directly connected to one another for treatment or processing such that the adjacent supporting bases cannot be moved relatively to each other in a longitudinal direction and/or in a transverse direction of the supporting base and
   the directly adjacent supporting bases are conveyed past the process station or through it together.

* * * * *